United States Patent
Lee

(10) Patent No.: US 10,530,999 B2
(45) Date of Patent: Jan. 7, 2020

(54) APPARATUS AND METHOD FOR PHOTOGRAPHING OBJECT USING TOP AND BOTTOM BUTTONS

(71) Applicant: OSSTEMIMPLANT CO., LTD., Seoul (KR)

(72) Inventor: Dong Yul Lee, Incheon (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 71 days.

(21) Appl. No.: 15/484,582

(22) Filed: Apr. 11, 2017

(65) Prior Publication Data
US 2017/0295320 A1 Oct. 12, 2017

(30) Foreign Application Priority Data
Apr. 12, 2016 (KR) .................. 10-2016-0044902

(51) Int. Cl.
*H04N 5/232* (2006.01)
*H04N 5/225* (2006.01)
*H04B 10/50* (2013.01)

(52) U.S. Cl.
CPC ....... *H04N 5/23245* (2013.01); *H04N 5/2252* (2013.01); *H04N 5/23241* (2013.01); *H04B 10/502* (2013.01); *H04N 2005/2255* (2013.01)

(58) Field of Classification Search
CPC ............. H04N 5/23245; H04N 5/2251; H04N 5/2252; H04N 5/23241; H04N 5/2253; H04N 2005/2255; H04N 5/2256; A61B 1/00039; A61B 1/247; A61B 1/0684; A61B 1/0676; A61B 1/05; A61B 1/00066; A61B 1/00055; A61B 1/00018; A61B 1/00016; A61B 1/00006; A61B 1/00027; H04B 10/502
See application file for complete search history.

(56) References Cited

U.S. PATENT DOCUMENTS

| 2008/0160477 A1 | 7/2008 | Stookey et al. |
| 2009/0023499 A1* | 1/2009 | Mao ............... G06F 13/387 |
| | | 463/39 |
| 2012/0009896 A1 | 1/2012 | Bandyopadhyay et al. |

(Continued)

FOREIGN PATENT DOCUMENTS

| CN | 103945756 A | 7/2014 |
| EP | 2614768 A1 | 7/2013 |

(Continued)

*Primary Examiner* — Joseph W Becker
(74) *Attorney, Agent, or Firm* — Novick, Kim & Lee, PLLC; Sang Ho Lee

(57) ABSTRACT

There are provided an apparatus and method for photographing an object. An apparatus for photographing an object using top and bottom buttons includes: a head part including a camera; a connection part coupled to the head part and extended in a length direction thereof, and having a first button for manipulating the camera on an extension line in the length direction from a formation position of the head part and a second button for manipulating the camera formed on a surface opposite to the first button; and a body part including a power source means coupled to the connection part and supplying power to the camera, and a display means displaying a state of the camera or a power state.

13 Claims, 6 Drawing Sheets

(56) References Cited

U.S. PATENT DOCUMENTS

| | | | |
|---|---|---|---|
| 2012/0219923 A1* | 8/2012 | Kert | A61C 19/004 |
| | | | 433/29 |
| 2013/0096457 A1* | 4/2013 | Qiu | A61B 1/267 |
| | | | 600/549 |
| 2013/0164567 A1* | 6/2013 | Olsson | H01M 10/488 |
| | | | 429/7 |
| 2013/0203010 A1 | 8/2013 | Inglese et al. | |
| 2013/0286174 A1* | 10/2013 | Urakabe | A61B 1/00009 |
| | | | 348/66 |
| 2017/0045806 A1* | 2/2017 | Tsuge | G03B 17/02 |

FOREIGN PATENT DOCUMENTS

| | | |
|---|---|---|
| JP | 2001-070225 A | 3/2001 |
| JP | 2004-237081 A | 8/2004 |
| JP | 2005-168520 A | 6/2005 |
| JP | 2010-514508 A | 5/2010 |
| JP | 2013-144110 A | 7/2013 |
| KR | 10-2012-0069794 A | 6/2012 |
| WO | 2013/010001 A1 | 1/2013 |

\* cited by examiner

APPARATUS AND METHOD FOR PHOTOGRAPHING OBJECT USING TOP AND BOTTOM BUTTONS

CROSS-REFERENCE TO RELATED APPLICATION

This application claims the priority and benefit of Korean Patent Application No. 10-2016-0044902 filed on Apr. 12, 2016, with the Korean Intellectual Property Office, the disclosure of which is incorporated herein by reference.

BACKGROUND OF THE INVENTION

1. Field of the Invention

The present invention relates to an apparatus and method for photographing an object.

2. Description of the Related Art

In the past, for a dental treatment, the dentist inserted a device having a mirror installed at a distal end into an oral cavity and checked a state of teeth reflected through the mirror to determine whether to treat or determine a treatment method.

The treatment using such a mirror had a problem that the patient may not directly check the state of teeth, and since the dentist checks the state of teeth with the naked eye through the reflection, there was a problem that it is difficult to perform a relatively accurate diagnosis.

Conventionally, a method was devised that a camera is miniaturized in accordance with the development of the technology of the camera and the dentist treats the patient by checking an image directly photographed by the camera.

However, the diagnosis device using the camera should transmit the image through wireless or wired communication with a main body installed at a dental chair. In the case of the wired connection scheme, since the diagnosis device, and a communication line and a power line for communication should be provided for each of the used main bodies, inconvenience due to additional components has been caused.

Accordingly, in the case of the wireless connection scheme, since communication interference with a plurality of chairs may occur, there is a need to separate channels, and there is a need to identify the patient by detecting a connection state with the main body through the diagnosis device.

In addition, since the conventional diagnosis device using the camera has a photographing button formed on only one side thereof, there is a problem in that a posture of the dentist becomes uncomfortable because the dentist has to turn his/her arm and photograph the teeth in order to alternately observe the teeth located on an upper jaw and a lower jaw.

SUMMARY

An aspect of the present invention may provide a configuration of a diagnosis device for providing an easier interface to alternately observe a state of the teeth located on an upper jaw and a lower jaw.

An aspect of the present invention may also provide a configuration that enables various diagnosis devices to be manipulated through an interface, and enables a user to easily recognize a manipulation state and a state of the diagnosis device accordingly.

An aspect of the present invention may provide a configuration for providing information for identifying a communication channel with a main body and a seamless communication state in a wireless communication scheme.

According to an aspect of the present invention, an apparatus for photographing an object using top and bottom buttons may include: a head part including a camera; a connection part coupled to the head part and extended in a length direction thereof, and having a first button for manipulating the camera on an extension line in the length direction from a formation position of the head part and a second button for manipulating the camera formed on a surface opposite to the first button; and a body part coupled to the connection part and including a power source means supplying power to the camera and a display means displaying a state of the camera or a power state.

The first button and the second button may be selectively operated, and a first camera control instruction may occur according to an operation of any one of the first button and the second button.

The first button and the second button may be independently operated, and a second camera control instruction may occur according to a simultaneous operation of the first button and the second button.

The first button and the second button may be independently operated, and a third camera control instruction may occur according to a sequential operation of the first button and the second button.

The apparatus may further include a communication unit for transmitting an image obtained from the camera to at least one main body, wherein the display means displays information for identifying a channel connection state between the communication unit and the main body.

The communication unit may be formed within the connection part, and be formed to be closer to the head part than the first or second button.

The display means may include a light emitting means for displaying a plurality of colors, and display information for identifying the channel connection state using a combination of the light emitting means.

The power source means may include a charge and discharge battery, and the display means may display a charged or discharged state of the charge and discharge battery.

The power source means may be supplied with power from an external power source, and the display means may display a power supply state of the external power source.

According to another aspect of the present invention, a method for controlling an object photographing apparatus using top and bottom buttons may include: receiving a power application instruction of a camera by an operation of at least one of a first button for manipulating the camera on an extension line in a length direction from a formation position of the camera and a second button for manipulating the camera formed on a surface opposite to the first button; receiving a control instruction of the camera by an operation of the first button or the second button; and transmitting an image obtained by the operation of the camera according to the control instruction to a main body.

The first button and the second button may be selectively operated, and a first camera control instruction may be received according to an operation of any one of the first button and the second button.

The first button and the second button may be independently operated, and a second camera control instruction may be received according to a simultaneous operation of the first button and the second button.

The first button and the second button may be independently operated, and a second camera control instruction may occur according to a sequential operation of the first button and the second button.

The method may further include identifying a control instruction according to an operation of the first button or the second button and displaying the identified control instruction.

In the displaying of the identified control instruction, a power state of the camera may be displayed.

In the displaying of the identified control instruction, information for identifying a channel connection state of the main body for transmitting the image in the transmitting of the image among a plurality of main bodies may be displayed.

DETAILED DESCRIPTION

The following description illustrates only a principle of the present invention. Therefore, those skilled in the art may implement the principle of the present invention and invent various apparatuses included in the spirit and scope of the present invention although not clearly described or shown in the present specification. In addition, it is to be understood that all conditional terms and exemplary embodiments mentioned in the present specification are obviously intended only to allow those skilled in the art to understand a concept of the present invention in principle, and the present invention is not limited to exemplary embodiments and states particularly mentioned as such.

The above-mentioned objects, features, and advantages will become more obvious from the following detailed description associated with the accompanying drawings. Therefore, those skilled in the art to which the present invention pertains may easily practice a technical idea of the present invention.

Further, in describing the present invention, in the case in which it is judged that a detailed description of a well-known technology associated with the present invention may unnecessarily make the gist of the present invention unclear, it will be omitted. Hereinafter, exemplary embodiments of the present invention will be described in detail with reference to the accompanying drawings.

Figure 1:
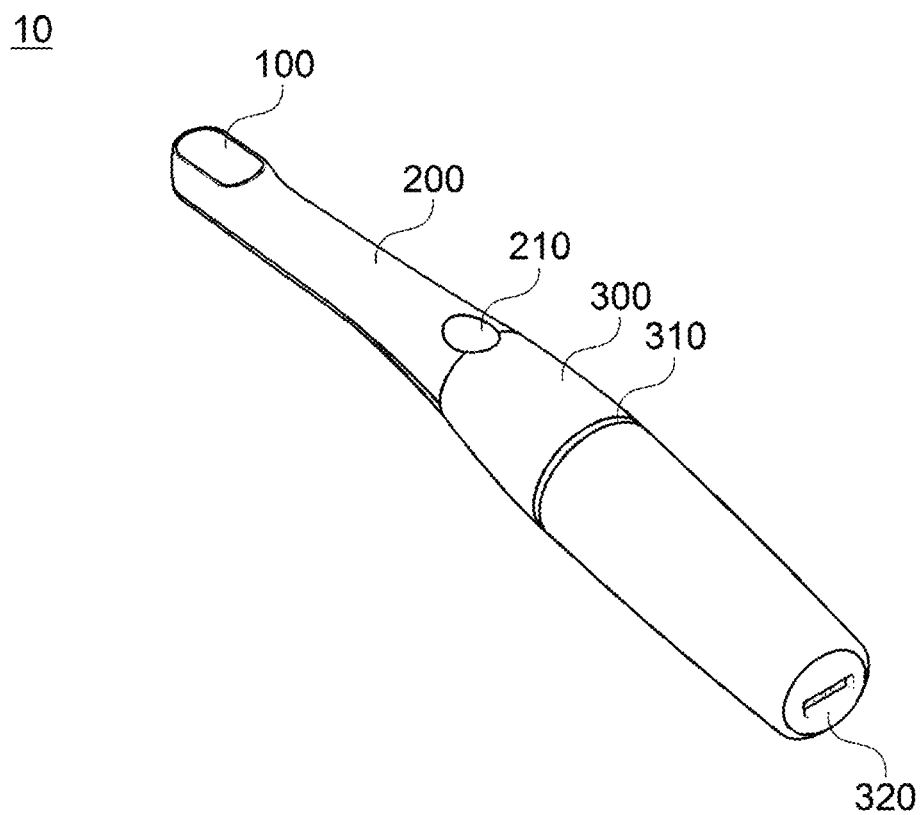
FIGS. 1 and 2 are diagrams illustrating an apparatus for photographing an object using top and bottom buttons according to an exemplary embodiment of the present invention.

FIG. 1 is a diagram illustrating an apparatus 10 for photographing an object (hereinafter, referred to as an object photographing apparatus) using top and bottom buttons according to an exemplary embodiment of the present invention.

Referring to FIG. 1, the object photographing apparatus 10 according to the present exemplary embodiment includes a head part 100, a connection part 200, and a body part 300.

The head part 100 includes a camera. The camera may photograph teeth, a set of teeth, and a state of a gum of a patient using a photographing element of a complementary metal oxide semiconductor (C-MOS) or a charge coupled device (CCD) camera.

In addition, the head part 100 may further include a lighting part. The lighting part is formed to more easily perform the photographing within an oral cavity of the patient in which light is relatively low, and according to the present exemplary embodiment, the lighting part may be a light emitting diode (LED) lamp.

In addition, although the present exemplary embodiment illustrates the object as the teeth, the set of teeth, and the gum of the patient, the object may also be any body portion of a subject, and accordingly, a photographing element of the camera and a configuration of the lighting part may also be changed.

According to the present exemplary embodiment, the connection part 200 is coupled to the head part 100 and extends in a length direction of the object photographing apparatus 10, a first button 210 for manipulating the camera is formed on an extension line in the length direction from a position at which the head part 100 is formed, and a second button 220 for manipulating the camera is provided on a surface opposite to the first button 210.

A tip of the connection part 200 is coupled to the head part 100 to have a shape having a length which is increased in the length direction.

A cross section of the connection part 200 has generally a circular or oval shape, and the first button 210 may be formed at the distal end of the extension line in the length direction based on a central portion of the head part 100 in a direction in which the head part 100 is coupled to the connection part 200.

The user may hold the object photographing apparatus 10 by positioning a thumb on the first button 210 while wrapping the body part 300 described below with a palm of hand.

Accordingly, the user may take a picture by inserting the head part into the oral cavity of the patient and pressing the first button 210.

Figure 2:
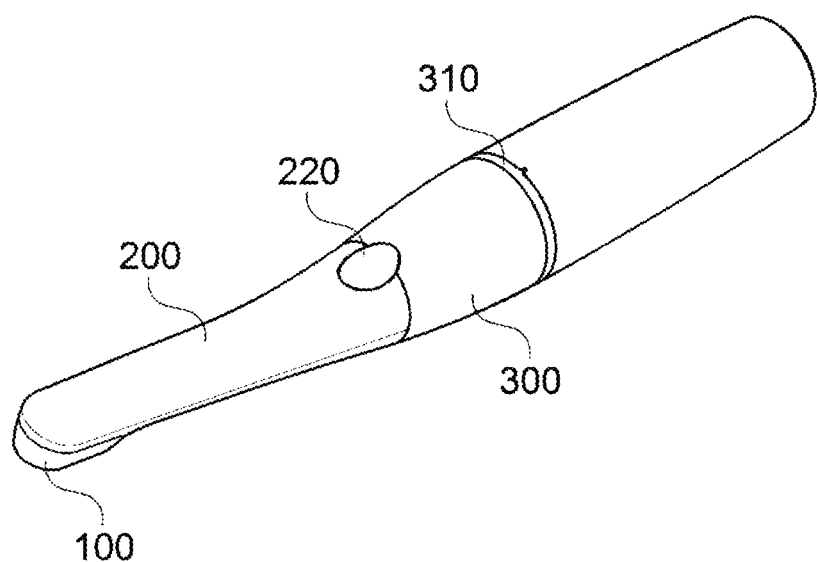

In addition, referring to FIG. 2, FIG. 2 is a diagram illustrating a rear surface of the object photographing apparatus 10 illustrated in FIG. 1, where the second button 220 may be formed on a surface opposite to the surface on which the first button 210 described above is formed.

Accordingly, the user may hold the object photographing apparatus 10 by positioning the thumb on the first button 210 and positioning an index finger on the second button 220.

Accordingly, the user may also take a picture by inserting the head part 100 into the oral cavity of the patient and pressing the second button 220.

According to the description above, the first button 210 and the second button 220 are formed in a direction opposite to each other with respect to a cross section of the connection part 200.

By using the second button 220, when the user photographs the lower jaw after photographing the upper jaw, it is possible to photograph the lower jaw using the thumb by turning-over the apparatus without twisting an arm.

According to the present exemplary embodiment, the first button 210 and the second button 220 are selectively operated, and it is possible to generate a first camera control instruction according to an operation of any one of the first button 210 and the second button 220.

Therefore, the first camera control instruction in this case may be an instruction that instructs to take a picture.

In addition, according to the present exemplary embodiment, since the first button 210 and the second button 220 may be simultaneously positioned on the thumb and the index finger of the user, respectively, it is also possible to generate a second camera control instruction according to a simultaneous operation of the first button 210 and the second button 220.

The second camera control instruction in this case may be an instruction that turns-on/off power of the camera.

In addition, it is also possible to subdivide the instruction by additionally using information about time at which the simultaneous operation is pressed.

For example, when the buttons are simultaneously pressed for 3 seconds in a state in which the camera is turned-off, the second camera control instruction that turns-on the camera may occur.

In addition, when the buttons are simultaneously pressed in a state in which the camera is turned-on, the second camera control instruction that turns-off the camera may occur.

Further, it is also possible to generate a third camera control instruction according to a sequential operation of the first button 210 and the second button 220 in addition to the simultaneous operation of the buttons.

For example, when the second button 220 is pressed within a predetermined time after the first button 210 is pressed, the camera is set to be zoomed in, and a result, a third camera control instruction that zooms in the camera may occur.

In contrast, when the first button 210 is pressed within a predetermined time after the second button 220 is pressed, the camera is set to be zoomed out, and the third camera control instruction that zooms out the camera may occur.

That is, according to the present exemplary embodiment, various objects may be photographed using the buttons positioned on both surfaces of the connection part 200 without the user twisting the arm, and various instructions may occur by adding a time variable to the operation of the button.

Next, according to the present exemplary embodiment, the body part 300 may be coupled to the connection part 200, and may include a power source means (not shown) for supplying power to the camera and a display means 310 for displaying a state of the camera or a state of the power.

Referring to FIG. 1 or 2, the body part 300 according to the present exemplary embodiment is coupled to the connection part 200 to configure a rear end of the object photographing apparatus 10.

The body part 300 may have a width thicker than that of the connection part 200 so that the user grasps the body part 300, and may include a power source means therein.

Specifically, when the object photographing apparatus 10 according to the present exemplary embodiment is connected in wired, examples of the power source means may include a wire for supplying the power to the camera and other modules and a circuit configuration for control.

In addition, when the object photographing apparatus 10 is wirelessly connected, a battery may be mounted as the power source means. In this case, the battery may be charged through a power connection terminal 320 formed in a rear end portion of the body part 300.

According to the present exemplary embodiment, the display means 310 may include an RGB LED to display various colors, through which more information may be provided to the user.

The information displayed by the display means 310 may be a turn-on/off state of the power.

In addition, when the object photographing apparatus 10 is wirelessly operated, information about a remaining amount of the battery may be displayed, and when the remaining amount of the battery of a predetermined level or less remains, it may also display that the charging is required.

In addition, the display means 310 may also be operated together with the lighting part formed on the head part 100 described above to provide additional information.

For example, when the camera is turned-on, the display means 310 and the lighting part may be operated together to inform the user that the object photographing apparatus 10 is turned-on.

Although not shown in FIGS. 1 and 2, the object photographing apparatus 10 according to the present exemplary embodiment may further include a communication unit (not shown).

According to the present exemplary embodiment, the object photographing apparatus 10 includes the communication unit for transmitting an image obtained from the camera to at least one main body 20.

That is, since the user or the patient checks a state of his/her own teeth and recognizes a treatment method or a need for a prescription through the image photographed by the camera, the image needs to be transmitted to the main body 20 including a display device such as a monitor.

The communication unit performs transmission of such an image to the main body. In addition, the communication unit may also transmit information set by the user to the object photographing apparatus 10.

Hereinafter, a method for connecting the object photographing apparatus 10 according to the present exemplary embodiment to the main body 20 will be described with reference to FIGS. 4 and 5.

Figure 4:
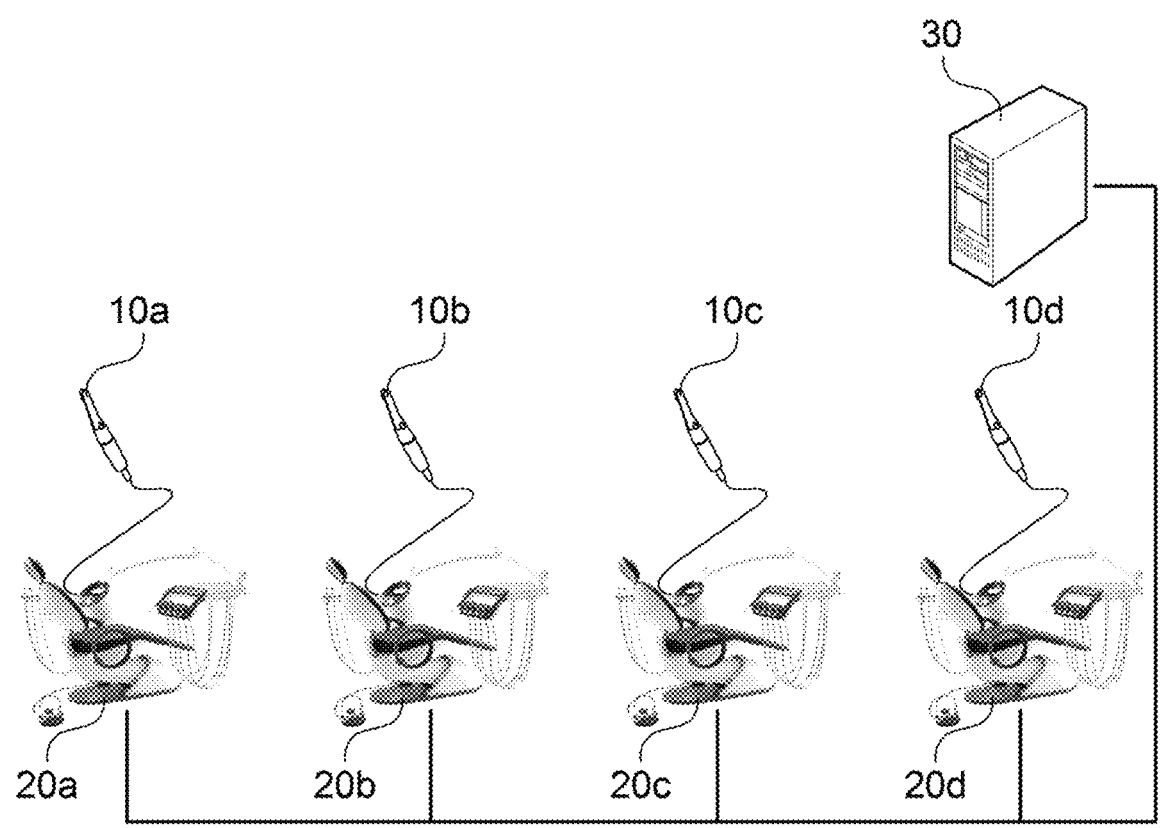
FIGS. 4 and 5 are diagrams illustrating a method for connecting the apparatus for photographing an object using top and bottom buttons according to an exemplary embodiment of the present invention to a main body.

Referring first to FIG. 4, FIG. 4 is a diagram illustrating a wired connection method.

Referring to FIG. 4, object photographing apparatuses 10a, 10b, 10c, and 10d according to the present exemplary embodiment are directly connected to the respective main bodies 20a, 20b, 20c, and 20d, are supplied with power using a connection line, and perform transmission and reception of information with the main body 20.

The received information is collected by a server 30, and the dentist stores and manages individual treatment information of patients using the collected information.

In this case, since the object photographing apparatus 10 is supplied with power through the main body 20, a separate battery is not required.

In addition, although FIG. 4 illustrates that the object photographing apparatus 10 is included in each of the main bodies, the object photographing apparatus 10 is configured to be detachable using the connection line and the connection terminal 320 illustrated in FIG. 1, and it is possible for the user to use one object photographing apparatus 10 by coupling one object photographing apparatus 10 to the connection line connected to the plurality of used main bodies.

Additionally, each of the main bodies may have a separate setting value, and in this case, the object photographing apparatus 10 may be connected to the connection line, read the separate setting value, and perform the photographing according to the setting value.

In this case, the separate setting value may be a setting value related to the camera such as focal information, brightness information, illumination information, and the like of the camera, and may include resolution information of the photographed image.

Figure 5:
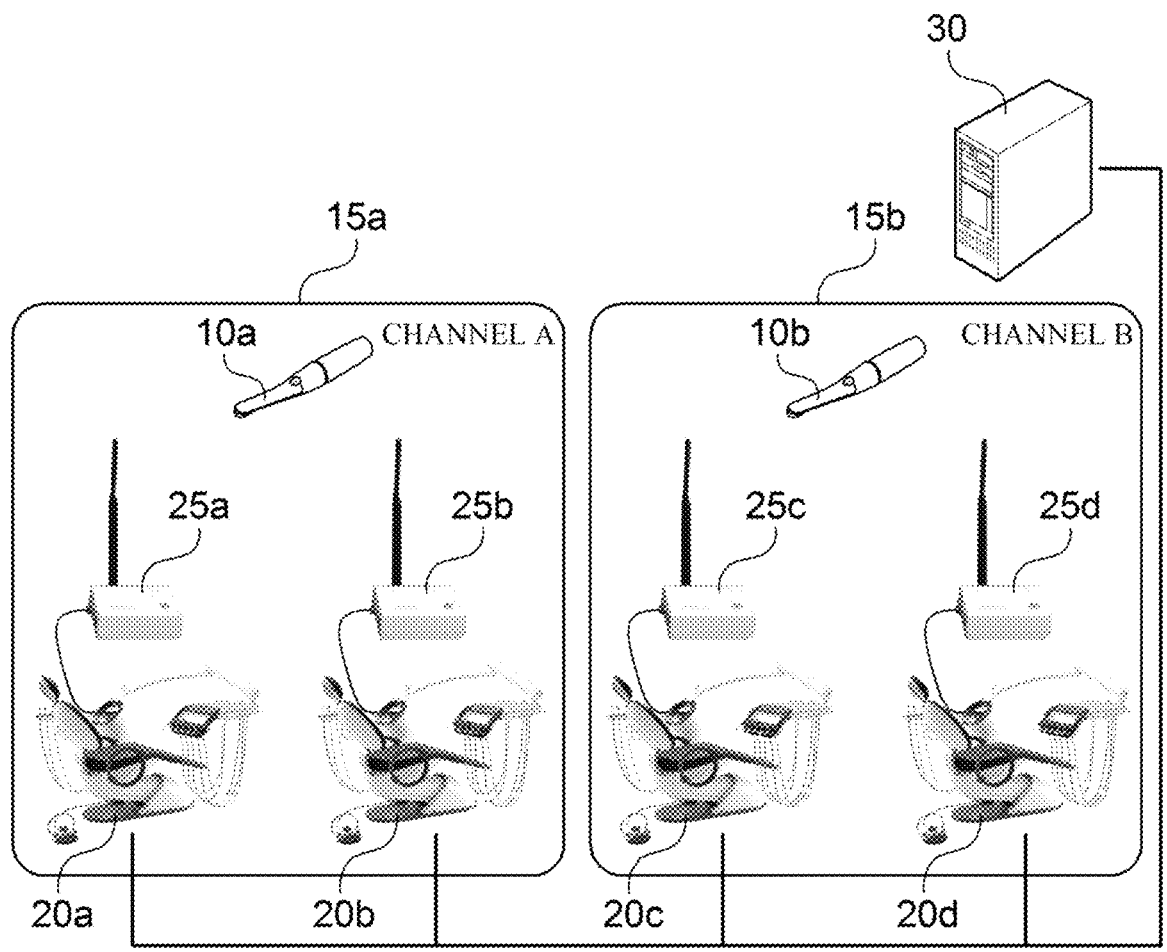

Referring next to FIG. 5, FIG. 5 illustrates that the object photographing apparatus 10 is connected to the main body 20 in a wireless communication scheme.

Referring to FIG. 5, receivers 25a, 25b, 25c, and 25d may be installed in or connected to the plurality of main bodies 20a, 20b, 20c, and 20d to enable wireless communication with the object photographing apparatuses 10a and 10b.

Accordingly, since image information obtained by the object photographing apparatus 10 is wirelessly transmitted to the main body 20, the communication unit may be configured as a wireless communication module.

The information received through the wireless communication is collected by the server 30, and the dentist stores and manages individual treatment information of patients using the collected information.

In this case, as the wireless communication method, Ultrawide Band (UWB), WiFi, and WiFi Direct (Widi) may be used.

Among UWB methods, in an environment in which only one object photographing apparatus 10 is used, it is easy to attach and detach one receiver to the used main body of the plurality of main bodies to be used.

Further, in an environment in which a plurality of object photographing apparatuses 10a and 10b are used, it is possible to attach and use a plurality of receivers 25a, 25b, 25c, and 25d to the main bodies 20a, 20b, 20c, and 20d within a group, and it is preferable to set channels to be different between other groups to prevent interference from occurring.

That is, in the case of the wireless communication method, when a plurality of users simultaneously use the plurality of object photographing apparatuses 10 in an environment in which there are a plurality of main bodies, mutual-interference may occur.

For example, when a plurality of dentists simultaneously perform the treatment, it is required to identify a connection between the object photographing apparatus 10 and the main body 20. Therefore, in this case, a problem such as transmission of the image to another object photographing apparatus 10, or the like may be prevented by grouping the main bodies and setting the channels 15a and 15b for each of the groups.

In this case, the display means 310 may display information for identifying a channel connection state between the communication unit and the main body.

Specifically, the object photographing apparatus 10 connected to the main bodies 20a and 20b belonging to a first group may be set so that a red LED of the display means 310 emits light, and the object photographing apparatus 10 connected to the main bodies 20c and 20d belonging to a second group may be set so that a blue LED of the display means 310 emits light.

Further, in the case in which wireless environment is established using WiFi, it is possible to communicate through a connection with a wireless LAN network of the WiFi regardless of the number of the main bodies, and in this case, the object photographing apparatus 10 may communicate by using each identification address set for each of the main bodies.

Additionally, it is also possible to communicate through Widi by connecting a wireless adapter (Dongle) to each of the respective main bodies in the WiFi environment.

In the above wireless communication environments, a formation position of the communication unit according to the present exemplary embodiment may be important.

The communication unit according to the present exemplary embodiment may be formed to be closer to the head part 100 than the first or second button 210 or 220.

That is, it is preferable that the formation position of the communication unit is closer to the head part 100 than at positions where the first button 210 and the second button 220 are formed.

According to the description described above, since the user wraps the body part 300 with the palm of the hand and positions the finger on the formation position of the button of the connection part 200, the communication unit may be blocked by the hand of the user when the communication unit is formed farther from the head part 100 than the formation position of the button, or is formed within the body part 300.

Specifically, the user may wrap an antenna of the communication unit according to a grasp form of the user, and in this case, a degradation of communication performance may occur.

Therefore, according to the present exemplary embodiment, the communication unit is formed to be closer to the head part 100 than the formation position of the button so as not to block the communication unit by the hand of the user.

However, in the case in which the communication unit is formed to be adjacent to the head part 100, since the communication unit enters the oral cavity of the patient together with the head part 100 on characteristics of the dental inspection, it is preferable that the communication unit is formed to be adjacent to the formation position of the button.

That is, the communication unit may be formed in the connection part 200 immediately above the buttons 210 and 220 formed at the most rear end with respect to the connection part 200.

Figure 3:
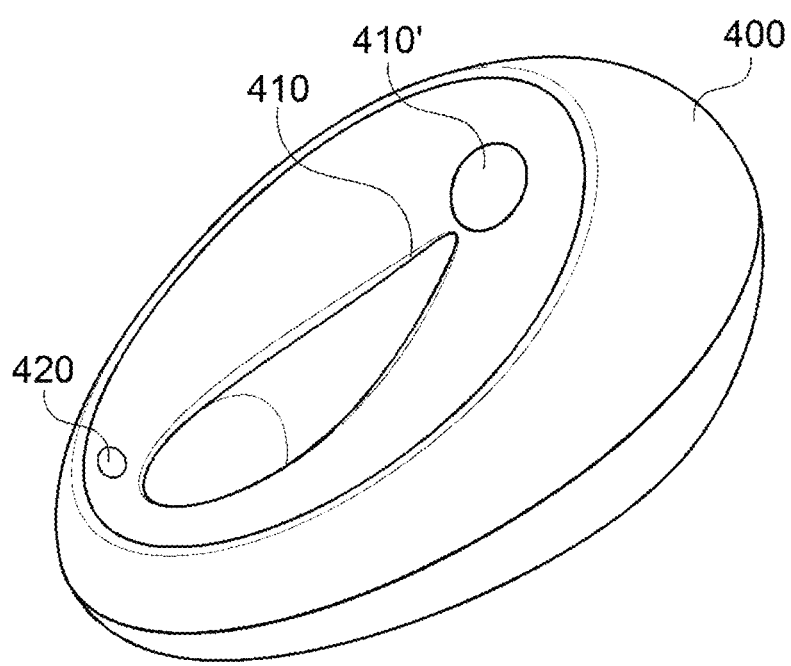
FIG. 3 is a diagram illustrating a cradle of the apparatus for photographing an object using top and bottom buttons according to an exemplary embodiment of the present invention.

Referring to FIG. 3, in the wireless scheme described above, the object photographing apparatus 10 may further include a cradle 400 for charging.

The cradle 400 may include cradling parts 410 and 410' on which the object photographing apparatus 10 is cradled, and a light emitting device as a display unit 420, and the display unit 420 may display a charge state of the object photographing apparatus 10.

For example, the display unit 420 may be turned-off when not fully charged, turn-on a red LED when being charged, turn-on a green LED at the time of the completion of charging, and turn-on/off the red LED at a time period when there is a problem in operation.

Hereinafter, a method for operating the object photographing apparatus 10 according to the present exemplary embodiment will be described.

Figure 6:
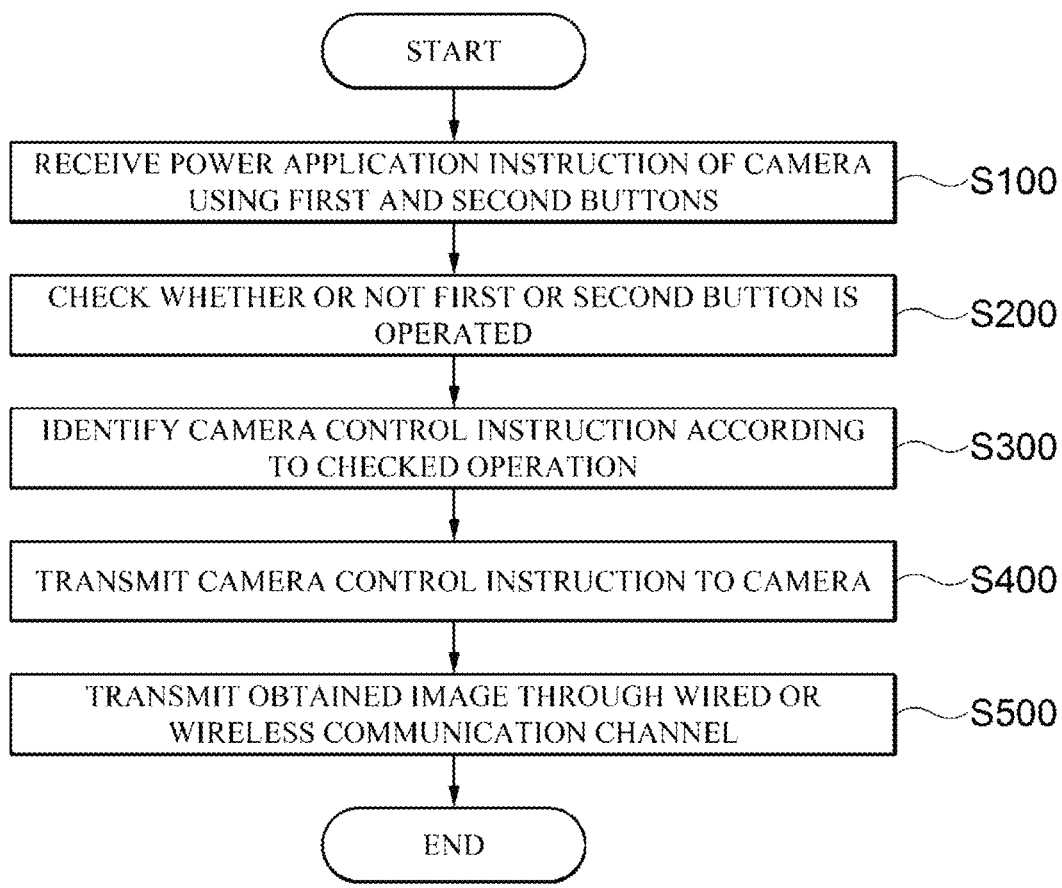
FIG. 6 is a diagram illustrating a method for controlling the apparatus for photographing an object using top and bottom buttons according to an exemplary embodiment of the present invention.

Referring to FIG. 6, a power application instruction of a camera is received by an operation of at least one operation of a first button 210 for manipulating the camera on an extension line in a length direction from a formation position of the camera or a second button 220 for manipulating the camera formed on a surface opposite to the first button 210 (S100).

According to the present exemplary embodiment, the power application instruction may occur according to a simultaneous operation of the first button 210 and the second button 220.

Accordingly, when the camera is turned-on, a control instruction of the camera is received by the operation of the first button 210 or the second button 220.

Specifically, the reception of the control instruction checks independently whether or not the first or second button 210 or 220 is operated (S200), and identifies one of the first to third camera control instructions described above according to the checked operation (S300).

The identified camera control instruction is transmitted to the camera (S400), and the camera obtains an image according to the control instruction.

The obtained image is transmitted to the main body through a wired or wireless communication channel (S500).

Additionally, although not shown, a state of the object photographing apparatus 10 according to each of the steps may be displayed to a user.

A display method thereof may be defined as Table 1 below.

TABLE 1

| Connection Scheme | Classification | Color | State | Note |
|---|---|---|---|---|
| Main Body <-> Wireless | Channel Display | Red, Yellow, Blue, Green | — | User Option |
| | Low Battery | Respective Colors | Continue Turn-On/Off | |
| | Power On | Respective Colors + Camera LED | Turn-On | Simultaneously Press Two Buttons for 3 Seconds Turn-off Camera LED After 5 Seconds |
| | Power Off | Respective Colors | Turn-Off after Turn-On/Off | Turn-On/Off Simultaneously with Pressing Two Buttons and Turn-Off After 3 Seconds Automatically Power Off When It Does Not Operate for 1 Minute |
| | Charging | Respective Colors | Turn-Off | Turn-Off after Slowly Turn-On/Off 5 times |
| Main Body <-> wired | — | Red, Yellow, Blue, Green | — | User Option |
| | Power On | Respective Colors + Camera LED | Turn-On | Automatically Power On When Cable Is Connected Simultaneously Press Two Buttons for 3 Seconds Turn-off Camera LED After 5 Seconds |
| | Power Off | Respective Colors | Turn-Off after Turn-On/Off 3 times | Turn-On/Off Simultaneously with Pressing Two Buttons and Turn-Off After 3 Seconds Automatically Power Off When It Does Not Operate for 1 Minute |
| Common | Shot | Respective Colors | Turn-On/Off once | |
| | Camera LED | — | Turn-Off | Turn-Off When It Does Not Operate for 10 Seconds Turn-On When Button Is Pressed |
| | Fail | Red, Yellow, Blue, Green | Continue Turn-On/Off | Turn-On While Respective Colors are Changed |

TABLE 1-continued

| Connection Scheme | Classification | Color | State | Note |
|---|---|---|---|---|
| Cradle | Charging Completion of Charging | Red Blue | Turn-On Turn-On | |

According to the exemplary embodiments of the present invention, a combination of various control instructions may be received by a combination of the buttons. Further, the user may easily check a state of the apparatus using a display unit by which a photographing state, a power state, etc., of the photographing apparatus may be checked.

Further, it is possible to distinguish the main body to which the user is currently connected by distinguishing channels for selectively connecting with a plurality of main bodies through a wireless communication scheme and displaying information for identifying the distinguished channel on the display unit.

According to the exemplary embodiments of the present invention, the state of the teeth located on the upper jaw and the lower jaw may be easily photographed using the buttons located on both surfaces of the photographing apparatus, and various control instructions may be input through a combination of the buttons. Further, the user may easily check a state of the apparatus using a display unit by which a photographing state, a power state, etc., of the photographing apparatus may be checked.

Further, it is possible to distinguish the main body to which the user is currently connected by distinguishing channels for selectively connecting with a plurality of main bodies through a wireless communication scheme and displaying information for identifying the distinguished channel on the display unit.

Further, it is possible to prevent a degradation of a communication state during a use of the apparatus by forming a communication unit for communicating with the main body at an open position.

The spirit of the present invention has been merely exemplified. It will be appreciated by those skilled in the art that various modifications and alterations can be made without departing from the essential characteristics of the present invention.

Accordingly, the exemplary embodiments disclosed in the present invention and the accompanying drawings do not limit but describe the spirit of the present invention, and the scope of the present invention is not limited by the exemplary embodiments and accompanying drawings. The scope of the present invention should be interpreted by the following claims and it should be interpreted that all spirit equivalent to the following claims fall within the scope of the present invention.

What is claimed is:

1. An apparatus for photographing an object using top and bottom buttons, the apparatus comprising:
   a head part including a camera;
   a connection part coupled to the head part and extended in a length direction thereof, and having a first button for manipulating the camera on an extension line in the length direction from a formation position of the head part and a second button for manipulating the camera formed on a surface opposite to the first button;

a body part coupled to the connection part and including a power source supplying power to the camera and a display displaying a state of the camera or a power state; and a communication unit for transmitting an image obtained from the camera to at least one main body, wherein a first camera control instruction that instructs to take a picture occurs when the first button and the second button are selectively operated; a second camera control instruction that instructs to set up the camera for taking a picture occurs when the first button and the second button are simultaneously operated; and a third camera control instruction that instructs to set up the camera for taking a picture and is different from the second camera control instruction occurs when one of the buttons is operated within a predetermined time after the other button is operated, wherein the display displays information for identifying a channel connection state between the communication unit and the main body, and wherein the apparatus is connected to the main body, and performs photographing according to a separate setting value related to one of focal information of the camera, brightness information of the camera, illumination information of the camera, and resolution information of the photographed image.

2. The apparatus of claim 1, wherein the second camera control instruction is an instruction that turns on or turns off power of the camera.

3. The apparatus of claim 1, wherein the third camera control instruction is an instruction that zooms in or zooms out the camera.

4. The apparatus of claim 1, wherein the display includes a light emitter for displaying a plurality of colors, and displays information for identifying the channel connection state using a combination of the light emitter.

5. The apparatus of claim 1, wherein the power source includes a charge and discharge battery, and the display displays a charged or discharged state of the charge and discharge battery.

6. The apparatus of claim 1, wherein the power source is supplied with power from an external power source, and the display displays a power supply state of the external power source.

7. The apparatus of claim 1, wherein the connection part has a cross section of circular or oval shape.

8. A method for photographing an object using top and bottom buttons, the method comprising:

receiving a power application instruction of a camera by an operation of at least one of a first button for manipulating the camera on an extension line in a length direction from a formation position of the camera and a second button for manipulating the camera formed on a surface opposite to the first button;

receiving a control instruction of the camera by an operation of the first button or the second button;

transmitting, by a communication unit, an image obtained by the operation of the camera according to the control instruction to a main body; and displaying on a display information for identifying a channel connection state between the communication unit and the main body, wherein a first camera control instruction that instructs to take a picture occurs when the first button and the second button are selectively operated; a second camera control instruction that instructs to set up the camera for taking a picture occurs when the first button and the second button are simultaneously operated; and a third camera control instruction that instructs to set up the camera for taking a picture and is different from the second camera control instruction occurs when one of the buttons is operated within a predetermined time after the other button is operated, wherein the image is obtained by photographing according to a separate setting value related to one of focal information of the camera, brightness information of the camera, illumination information of the camera, and resolution information of the photographed image.

9. The method of claim 8, wherein the second camera control instruction is an instruction that turns on or turns off power of the camera.

10. The method of claim 8, wherein the third camera control instruction is an instruction that zooms in or zooms out the camera.

11. The method of claim 8, wherein the connection part has a cross section of circular or oval shape.

12. The method of claim 8, further comprising:

identifying a control instruction according to an operation of the first button or the second button and displaying the identified control instruction.

13. The method of claim 12, wherein in the displaying of the identified control instruction, information for identifying a channel connection state of the main body for transmitting the image in the transmitting of the image among a plurality of main bodies is displayed.

* * * * *